United States Patent [19]

Bugaut et al.

[11] Patent Number: 5,186,717
[45] Date of Patent: Feb. 16, 1993

[54] DYEING COMPOSITIONS FOR KERATIN FIBRES, BASED ON 3-NITRO-ORTHO-PHENYLENEDIAMINES, AND CERTAIN 3-NITRO-ORTHO-PHENYLENEDIAMINES USED THEREIN

[75] Inventors: Andree Bugaut, Boulogne-Billancourt; Alex Junino; Jean J. Vandenboosche, both of Aulnay-sous-Bois, all of France

[73] Assignee: L'Oreal, Paris, France

[21] Appl. No.: 764,958

[22] Filed: Sep. 25, 1991

Related U.S. Application Data

[63] Continuation of Ser. No. 124,433, Nov. 23, 1987, abandoned, which is a continuation of Ser. No. 339,141, Jan. 13, 1982, abandoned.

[30] Foreign Application Priority Data

Jan. 14, 1981 [LU] Luxembourg ................ 83063

[51] Int. Cl.$^5$ ................ A61K 7/13; A61K 7/135; A61K 9/12
[52] U.S. Cl. ............................... 8/405; 8/415; 8/428; 8/662; 8/675; 132/208; 424/47
[58] Field of Search ...................... 8/405, 415, 428

[56] References Cited

U.S. PATENT DOCUMENTS

| | | | |
|---|---|---|---|
| 2,750,326 | 6/1956 | Eckardt | 8/408 |
| 3,743,678 | 7/1973 | Halasz | 8/415 |
| 3,929,404 | 12/1975 | Kalopissis et al. | 8/407 |
| 3,930,792 | 1/1976 | Alperin et al. | |
| 3,933,886 | 1/1976 | Saygin | 8/415 |
| 3,973,900 | 8/1976 | Husemeyer et al. | 8/407 |
| 4,007,747 | 2/1977 | Kalopissis et al. | 8/497 |
| 4,008,999 | 2/1977 | Kalopissis et al. | |
| 4,023,926 | 5/1977 | Bugaut et al. | 8/407 |
| 4,200,432 | 4/1980 | Kalopissis et al. | |

FOREIGN PATENT DOCUMENTS

| | | |
|---|---|---|
| 707618 | 4/1954 | United Kingdom . |
| 1080154 | 7/1967 | United Kingdom . |
| 1187534 | 4/1970 | United Kingdom . |

OTHER PUBLICATIONS

Zhurnal Organicheskoi Khimil, vol. 10, No. 9, Sep. 1974, pp. 1927-1930 D. D. Mysk et al: "Acyl derivatives of arylenediamines. IV. Nitration and hydrolisis of N,N'-diacyl- and triacyl-o-phenylenediamines.", Plenum Publ.

Chemical Abstracts, vol. 82, No. 3, Jan. 20, 1975, ref. No. 16506y, p. 469 Colombus, Ohio.

E. Richter: Beilsteins Handbuch der Organischen Chemie, Fourth Edition vol. 13, J. Springer, 1933, p. 10, Berlin (DE).

Chemical Abstracts, vol. 80, No. 23, Jun. 1974, ref. No. 133343n, p. 474 Colombus, Ohio.

Synthesis, International Journal of Methods in Synthetic Organic Chemistry, No. 10, Oct. 1974, R. E. Lyle et al: "Selective Rapid Transfer-hydrogenation of 2,6-Dinitroanilines", pp. 726-727, Stuttgart (DE).

Journal of the Chemical Society, Perkin Transactions I, Organic and Bio-Organic Chemistry, 1975, I. D. Entwistle et al: "Selective Rapid Transfer-hydrogenation of Aromatic Nitro-compounds.", pp. 1300-1301.

J. Org. Chem., pp. 438-441, (1975).

Primary Examiner—Dale R. Ore
Attorney, Agent, or Firm—Jacobson, Price, Holman & Stern

[57] ABSTRACT

The invention provides dyeing compositions for keratin fibres, which contain at least one dyestuff corresponding to the formula:

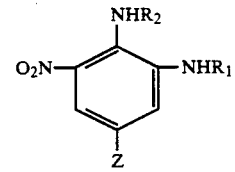

in which $R_1$ and $R_2$ independently of one another denote a hydrogen atom, an alkyl group, a monohydroxyalkyl or polyhydroxyalkyl group, an alkyl group substituted by an alkoxy group, or an aminoalkyl group of which the amino group can optionally be monosubstituted or disubstituted by an alkyl group, and the radical $R_2$ can also denote a phenyl group or a phenyl group substituted by an alkyl, hydroxyl or amino group, and Z denotes a hydrogen atom or an alkyl group, or their cosmetically acceptable salts. Many of the dyestuffs are novel.

16 Claims, No Drawings

DYEING COMPOSITIONS FOR KERATIN FIBRES, BASED ON 3-NITRO-ORTHO-PHENYLENEDIAMINES, AND CERTAIN 3-NITRO-ORTHO-PHENYLENEDIAMINES USED THEREIN

This application is a continuation, of application Ser. No. 124,433, filed Nov. 23, 1987, now abandoned, which is a continuation of application Ser. No. 339,141, filed Jan. 13, 1982, now abandoned.

As is well known, keratin fibres, and in particular human hair, are frequently given a direct colouration, or a complementary sheen in the case of oxidation colouration, using nitro derivatives of the benzene series. We have discovered that, to give keratin fibres red shades, it is possible to use nitro-ortho-phenylenediamines, contrary to expectations. This is particularly surprising since it is known that 4-nitro-ortho-phenylenediamine gives rise to yellow colourations.

We have found that the hair dyes obtained with the aid of this class of dyestuffs have a good stability to light.

Furthermore, these dyestuffs have the advantage of being only slightly selective or non-selective. As is well known, selectivity is an important practical problem in the field of hair dyeing because of the different sensitisation of the hair from the root to the tip. In fact, hairdressers generally deal with hair of which the sensitisation is virtually zero for the freshly grown root, strong for the parts treated earlier, which have undergone colouration, bleaching or perming, and very strong for the tips, which have undergone several of these treatments and which are exposed daily to light and adverse weather conditions.

We have discovered that the class of 3-nitro-ortho-phenylenediamines selected makes it possible to obtain intensities of colouration which are substantially similar whether or not the hair is permed.

We have also found that the dyestuffs used according to the invention are particularly stable in oxidation dyeing carriers and in particular in an ammoniacal medium, in the presence of reducing agents, and this makes it possible for them to be associated with so-called oxidation dyestuffs in order to obtain shades with a rich sheen.

The present invention thus relates to dyeing compositions for keratin fibres, containing certain 3-nitro-ortho-phenylenediamines, as well as to new 3-nitro-ortho-phenylenediamines used according to the invention, and also processes for their preparation.

The dyeing compositions for keratin fibres, according to the invention, are essentially characterised in that they contain, in a solvent medium suitable for dyeing keratin fibres, at least one dyestuff corresponding to the formula:

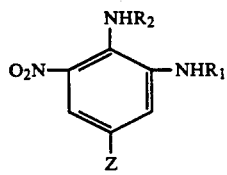

(I)

in which $R_1$ and $R_2$ independently of one another denote a hydrogen atom, an alkyl group, a monohydroxyalkyl or polyhydroxyalkyl group, an alkyl group substituted by an alkoxy group, or an aminoalkyl group of which the amino group can optionally be monosubstituted or disubstituted by an alkyl group, and the radical $R_2$ can also denote a phenyl group or a phenyl group substituted by an alkyl, hydroxyl or amino group, and Z denotes a hydrogen atom or an alkyl group.

In the abovementioned formula, the alkyl radical preferably denotes a radical having from 1 to 4 carbon atoms and the alkoxy group preferably denotes methoxy or ethoxy.

Amongst the more particularly preferred groups, there may be mentioned, in the case of $R_2$, a hydrogen atom, a methyl, ethyl, propyl or butyl group, a β-hydroxyethyl group, a β-hydroxypropyl group, a β,γ-dihydroxypropyl group, an N,N-diethylaminoethyl group, a p-hydroxyphenyl group or a β-methoxyethyl group, in the case of $R_1$, a hydrogen atom or a methyl, ethyl or β-hydroxyethyl group, and in the case of Z, a hydrogen atom and a methyl group.

The compounds which give particularly advantageous results within the scope of the present invention correspond to the formula (I) in which Z necessarily denotes a methyl group. Other compounds which give particularly valuable results are those in which $R_2$ is different from hydrogen and denotes, in particular, methyl or β-hydroxyethyl. In particular, these compounds are very harmless.

These compounds can also be used in the form of their cosmetically acceptable salts, such as in the form of the hydrochloride or sulphate.

The preferred compounds used according to the invention make it possible to obtain coppery shades which are more or less rich in red, ranging from 7.5 YR to 10 R on the Munsell scale.

The shade is denoted by H in Munsell's notation, according to which a colour is defined by the formula HV/C, in which the three parameters respectively denote the shade or "hue" (H), the intensity of "value" (V) and the purity or "chromaticity" (C), the oblique line being simply a convention.

For Munsell's notation, reference may be made to "Official Digest", April 1964, pages 373 to 377.

Amongst the compounds which can be used according to the invention, the compounds of the formula (II):

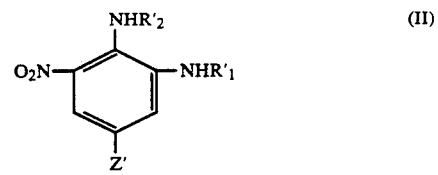

(II)

in which $R'_1$ and $R'_2$ independently of one another denote a hydrogen atom, an alkyl group, a monohydroxyalkyl or polyhydroxyalkyl group, an alkyl group substituted by an alkoxy group, or an aminoalkyl group of which the amino group can optionally be monosubstituted or disubstituted by an alkyl group, and the radical $R'_2$ can also denote a phenyl group or a phenyl group substituted by an alkyl, hydroxyl or amino group, and $Z'$ denotes a hydrogen atom or an alkyl group, with the proviso that $R'_1$, $R'_2$ and $Z'$ cannot simultaneously denote hydrogen, if $R'_2$ denotes methyl or phenyl, $R'_1$ and $Z'$ cannot simultaneously denote hydrogen, if $Z'$ denotes methyl, at least one of the groups $R'_1$ or $R'_2$ is different from hydrogen, and if R'₁ and R'₂ denote methyl, Z' is different from hydrogen, and their cosmetically acceptable salts, are new.

The compounds of the formula (I) in which $R_1$ denotes hydrogen can be prepared by selectively reducing the compounds of the formula (III):

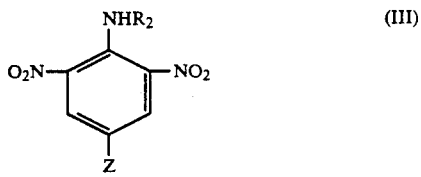

the selective reduction being carried out either with the aid of alkaline sulphite, according to M. Kamel, M. I. Ali and M. M. Kamel, Tetrahedron 1966, Volume 22, page 3,353, or by hydrogen transfer from cyclohexene to the compound of the formula (III), in the presence of palladium-on-charcoal as a catalyst, according to Ian D. Entwistle, Robert A. W. Johnstone and T. Jeffery Povall, JCS Perkin I 1975, page 1,300.

The compounds of the formula (I) in which $R_1$ denotes alkyl or substituted alkyl can be obtained by selective benzenesulphonation or para-toluenesulphonation of the compounds of the formula (I) in which $R_1$ denotes hydrogen. A halogenoalkane of the formula $XR_1$, in which X denotes a halogen atom and $R_1$ denotes alkyl or substituted alkyl, can then be reacted with the arylsulphonamides thus obtained, and then, after substitution, the sulphonamides hydrolysed.

The reaction scheme can essentially be summarised in the following way:

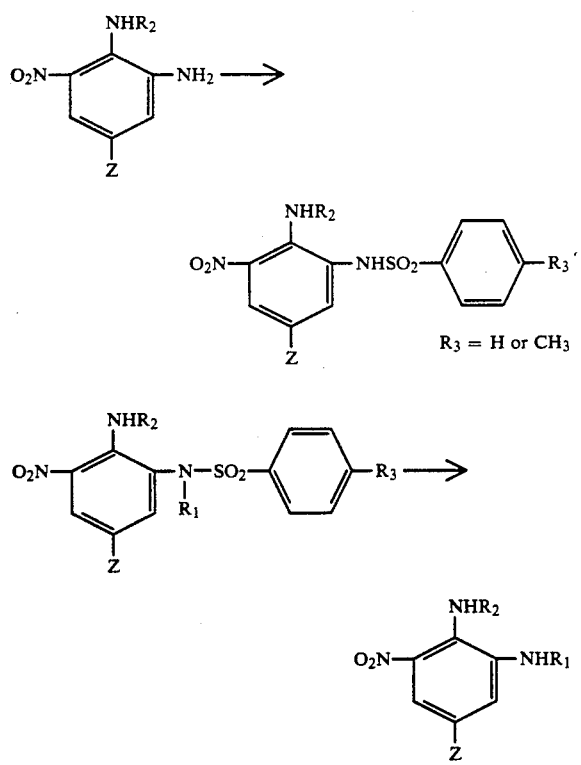

A certain number of the intermediates of the formula (III), used in this process of the invention, are in themselves known. In general, these compounds of the formula (III) can be obtained by reacting ammonia or amines of the formula $R_2NH_2$, in which $R_2$ has the same meaning as that indicated above, with the chlorinated or methoxylated dinitro compounds, taking advantage of the mobility of the chlorine atom or of the methoxy group.

The compositions according to the invention can be used for the direct colouration of keratin fibres, or for the oxidation colouration of these fibres, in which case the compounds of the formula (I) impart a complementary sheen to the base colouration obtained by oxidising development of the oxidation dyestuff precursors. These compositions suitably contain the compounds of the formula (I) in concentrations of 0.001 to 5% by weight and preferably 0.01 to 3% by weight, relative to the total weight of the dyeing composition.

These compositions can contain anionic, cationic, non-ionic or amphoteric surface-active agents or mixtures thereof. These surface-active products are typically present in the compositions of the invention in concentrations of 0.5 to 55% by weight and preferably 4 to 40% by weight, relative to the total weight of the composition.

The cosmetic vehicle generally consists of water, and organic solvents can also be added to the compositions in order to solubilise compounds which would not otherwise be sufficiently soluble in water. Amongst these solvents, there may be mentioned lower alkanols, typically of 1 to 6 carbon atoms, such as ethanol and isopropanol, polyols such as glycerol, glycols or glycol ethers, such as 2-butoxyethanol, ethylene glycol, ethylene glycol monoethyl ether, propylene glycol, and diethylene glycol monoethyl ether, and monomethyl ether and also mixtures thereof. These solvents are preferably present in concentrations from 1 to 75% by weight and in particular from 5 to 50% by weight, relative to the total weight of the composition.

The compositions can be thickened, preferably with sodium alginate, gum arabic, cellulose derivatives such as methylcellulose, hydroxyethylcellulose, hydroxypropylmethylcellulose and carboxymethylcellulose, or various polymers acting as thickeners, more particularly acrylic acid derivatives. It is also possible to use inorganic thickeners such as bentonite. These thickeners are preferably present in concentrations of 0.5 to 10% by weight and in particular 0.5 to 3% by weight, relative to the total weight of the composition.

The compositions according to the invention can also contain various adjuvants normally used in hair-dyeing compositions, and in particular, penetrating agents, sequestering agents, film-forming agents, buffers, preservatives and perfumes.

These compositions can be presented in various forms such as liquids, creams or gels, or in any other form suitable for dyeing the hair. They can also be packaged in aerosol flasks in the presence of a propellant.

The pH of these dyeing compositions is generally 3 to 11.5, preferably 5 to 11.5. It can be adjusted to the desired value with the aid of an alkalising agent such as ammonia, sodium carbonate, potassium carbonate or ammonium carbonate, sodium hydroxide or potassium hydroxide, alkanolamines such as mono-, di- or triethanolamine, or alkylamines such as ethylamine or triethylamine, or with the aid of an acidifying agent such as phosphoric, hydrochloric, tartaric, acetic, lactic or citric acid.

If the compositions are intended for use in a process for direct colouration of the hair, they can contain, in addition to the compounds according to the invention, other direct dyestuffs such as azo dyestuffs or anthraquinone dyestuffs, for example, tetraaminoanthraquinone, and nitro dyestuffs of the benzene series other than the compounds of the formula (I), and more particularly the following compounds: 2-methyl-6-nitroaniline, 3-nitro-4-aminophenol, 3-nitro-4-N-($\beta$-hydroxyethyl)-aminophenol, 3-nitro-4-amino-6-methylphenol, 3-amino-4-nitrophenol, 2-amino-3-nitrophenol, 3-nitro-6-N-($\beta$-hydroxyethyl)-aminoanisole, 3-N-($\beta$,$\gamma$-dihydroxypropyl)amino-4-nitroanisole, 3-N-methylamino-4-nitrophenoxyethanol, 3-N-methylamino-4-nitrophenyl $\beta$,$\gamma$-dihydroxypropyl ether, N,N'-($\beta$-hydroxyethyl)-nitro-para-phenylenediamine, 3-nitro-4-N'-methylamino-N,N-di-($\beta$-hydroxyethyl)aniline, 2-methyl-4-amino-5-nitro-N-($\beta$-hydroxyethyl)aniline, 2-methyl-4-amino-5-nitro-N-($\beta$-diethylaminoethyl)aniline and 2-methyl-4-amino-5-nitro-N-methylaniline. The concentrations of these direct dyestuffs other than the dyestuffs of the formula (I) is suitably 0.001 to 5% by weight, relative to the total weight of the composition.

These compositions are applied to the keratin fibres for, say, 5 to 70 minutes and the fibres are then rinsed, if appropriate washed and rinsed again, and dried.

These compositions can also be used in the form of a wavesetting hair lotion intended both to give the hair a slight colouration and to improve the hold of the hair. In this case, they are presented in the form of aqueous, alcoholic or aqueous-alcoholic solutions containing at least one cosmetic resin; they can be applied to damp hair which has been washed and rinsed beforehand, and the hair is wound onto rollers, if appropriate, and then dried.

The cosmetic resins used in the wavesetting lotions can be, in particular, polyvinylpyrrolidone, crotonic acid/vinyl acetate and vinylpyrrolidone/vinyl acetate copolymers, half-esters of maleic anhydride/butyl vinyl ether and maleic anhydride/methyl vinyl ether copolymers, and also other cationic, anionic, non-ionic or amphoteric polymers used in this type of composition. These cosmetic resins are generally present in the compositions of the invention in amounts of 1 to 3% by weight and preferably of 1 to 2% by weight, based on the total weight of the composition.

If the compositions constitute oxidation dyes, the compounds of the formula (I), according to the invention, are essentially used in order to impart a sheen to the final dyeing. In this case, these compositions contain oxidation dyestuff precursors, in association with at least one nitro dyestuff of the formula (I).

These compositions can contain, for example, para-phenylenediamines such as: para-phenylenediamine, para-toluylenediamine, 2,6-dimethyl-para-phenylenediamine, 2,6-dimethyl-3-methoxy-para-phenylenediamine, N-($\beta$-methoxyethyl)-para-phenylenediamine, 4-N,N-di-($\beta$-hydroxyethyl)aminoaniline and 4-(N-ethyl-N-carbamylmethyl)-aminoaniline, and also their salts.

They can also contain para-aminophenols, for example: para-aminophenol, N-methyl-para-aminophenol, 2-chloro-4-aminophenol, 3-chloro-4-aminophenol and 2-methyl-4-aminophenol, and their salts.

They can also contain heterocyclic derivatives, for example: 2,5-diaminopyridine, 5-N,N-diethylamino-2-aminopyridine, 7-aminobenzomorpholine and 2-amino-5-hydroxypyridine.

The compositions according to the invention can contain, in association with the oxidation dyestuff precursors "of the para type", couplers which are well known in the state of the art.

Couplers which may be mentioned in particular are: meta-diphenols such as resorcinol and 2-methylresorcinol, meta-aminophenols such as: meta-aminophenol, 2-methyl-5-aminophenol, 2-methyl-5-N-($\beta$-hydroxyethyl)-aminophenol and 6-hydroxybenzomorpholine, and their salts, meta-phenylenediamines such as: 2,4-diaminophenoxyethanol, 2,4-diaminophenyl $\beta$-aminoethyl ether, 6-aminobenzomorpholine, 2-N-($\beta$-hydroxyethyl)-amino-4-aminophenoxyethanol and 2,4-diaminophenyl $\beta$,$\gamma$-dihydroxypropyl ether, and their salts, and meta-acylaminophenols, meta-ureidophenols and meta-carbalkoxyaminophenols, such as: 2-methyl-5-acetylaminophenol, 2-methyl-5-ureidophenol and 2-methyl-5-carbethoxyaminophenol.

Finally, the following may be mentioned as other couplers which can be used in the compositions of the invention: $\alpha$-naphthol, couplers possessing an active methylene group, such as diketone compounds and pyrazolones, and heterocyclic couplers such as 2,4-diaminopyridine, and also their salts.

In addition to the oxidation dyestuff precursors, these compositions can contain reducing agents such as sodium sulphite, thioglycolic acid, thiolactic acid, sodium bisulphite, ascorbic acid and hydroquinone. These reducing agents are typically present in concentrations of 0.5 to 1.5% by weight, relative to the total weight of the composition. The oxidation dye-stuff precursors are suitably used in the compositions of the invention at concentrations of 0.001 to 5% by weight and preferably 0.03 to 2% by weight, based on the total weight of the composition. The couplers can also be present in concentrations of 0.001 to 5% by weight, preferably 0.015 to 2% by weight. The pH of the compositions is preferably 7 to 11.5 and can be adjusted with the aid of alkalising agents mentioned above.

We have found that the compounds of formula (I) are particularly stable in such compositions.

The process for dyeing keratin fibres, in particular human hair, using development by an oxidising agent, consists in applying, to the hair, the dyeing composition comprising both a dyestuff according to the invention and the oxidation dyestuff precursors, and in developing the colouration with the aid of an oxidising agent which is present in the dyeing composition or which is applied to the hair in a second stage.

The oxidising agent is preferably hydrogen peroxide, urea peroxide or a per-salt. A solution of hydrogen peroxide of 20 volumes strength can be used in particular.

Once the composition, with the oxidising agent has been applied to the keratin fibres, it is left on the fibres for, say, 10 to 50 minutes, preferably 15 to 30 minutes, after which the keratin fibres are rinsed, if appropriate shampooed and rinsed again, and dried.

The following Examples further illustrate the present invention.

EXAMPLE 1

The following dyeing composition is prepared:

| | |
|---|---|
| 2-Amino-3-nitro-5-methyl-N-methylaniline | 0.9 g |
| 2-Butoxyethanol | 10 g |
| Alfol $C_{16}/_{18}$ (50/50) | 8 g |
| Lanette wax | 0.5 g |
| Cemulsol B | 1 g |
| Oleic diethanolamide | 1.5 g |

-continued

| | |
|---|---|
| Triethanolamine | 1 g |
| Water q.s.p. | 100 g |

This composition has a pH of 9.

When applied to bleached hair for 25 minutes at 28° C., this mixture imparts to the hair, after rinsing and shampooing, a colouration of 2.0 YR 5.5/8 on the Munsell scale.

The compositions mentioned in Table 1 which follows are prepared in the same way as that indicated above, the carrier being the same as that used in Example 1 and the alkalising agent being specified, together with the pH. The dyeing conditions, such as the temperature, the rinsing and the washing, are similar to those indicated in Example 1. An amount of water sufficient for 100 g of composition is always added.

On applying the composition of Example 2 to 90% naturally white hair permed beforehand, and otherwise following the same procedure, a colouration of 7.5 YR 6/8 on the Munsell scale is found, which is identical to that observed on 90% naturally white hair dyed under the same conditions.

TABLE I

| EX-AM-PLE | DYESTUFF | | COMPOSITIONS | | |
|---|---|---|---|---|---|
| | | % g | alkalising agent | % g | pH |
| 1 | 2-amino-3-nitro-5-methyl-N-methyl-aniline | 0.9 | triethanolamine | 1 | 9 |
| 2 | 3-nitro-ortho-phenylenediamine | 0.35 | triethanolamine | 1 | 9 |
| 3 | 2-N-methylamino-3-nitroaniline | 1 | 22° B strength ammonia solution | 1 | 10.6 |
| 4 | 2-N-($\beta$-hydroxyethyl)-amino-3-nitroaniline | 2 | 22° B strength ammonia solution | 1 | 10.6 |
| 5 | 2-amino-3-nitro-N-methylaniline | 2 | 22° B strength ammonia solution | 2 | 11 |
| 6 | 2-amino-3-nitro-N-methylaniline | 1 | 22° B strength ammonia solution | 1 | 10.5 |
| | 2-N-($\beta$-hydroxyethyl)-amino-3-nitroaniline | 1 | | | |
| | tetraaminoanthraquinone | 0.25 | | | |
| 7 | 2-N-methylamino-3-nitroaniline | 1.2 | | | 7.5 |
| | N,N'-($\beta$-hydroxyethyl)-nitro-p-phenylenediamine | 0.31 | | | |
| | tetraaminoanthraquinone | 0.4 | | | |
| 8 | 2-N-methylamino-3-nitro-5-methyl-aniline | 0.25 | 22° B strength ammonia solution | 0.8 | 10 |
| 9 | 2-(4'-hydroxyphenyl)-amino-3-nitro-5-methylaniline | 0.35 | monoethanolamine | 1 | 10 |

| | DYEING | | |
|---|---|---|---|
| EXAMPLE | Application time | Bleached hair | 90% naturally white hair |
| 1 | 25 minutes | 2 YR 5.5/8 | |
| 2 | 30 | | 7.5 YR 6/8 |
| 3 | 30 | | 7.5 YR 6/9 |
| 4 | 20 | 5 YR 6/11 | |
| 5 | 25 | 10 R 5/10 | 1.5 YR 4/8 |
| 6 | 25 | | 5 YR 4/7 |
| 7 | 25 | | 3 YR 4/3 |
| 8 | 30 | 6 YR 7/4 | |
| 9 | 30 | 6 YR 8/4 | |

EXAMPLE 10

The following dyeing composition is prepared:

| | |
|---|---|
| 2-Amino-3-nitro-5-methyl-N-methylaniline | 0.5 g |
| 3-Nitro-4-N'-methylamino-N-($\beta$-aminoethyl)-aniline | 0.1 g |
| 3-N-Methylamino-4-nitrophenoxyethanol | 0.28 g |
| 96° strength ethanol | 5 g |
| Propylene glycol | 5 g |
| Diethanolamides of copra fatty acids | 2.2 g |
| Lauric acid | 0.8 g |
| Ethylene glycol monoethyl ether | 2 g |
| Monoethanolamine | 1.1 g |
| Water q.s.p. | 100 g |
| pH 10.5 | |

When applied for 25 minutes at 30° C. to hair which has been bleached white, this mixture imparts to the hair, after rinsing and shampooing, a light copper-red colouration.

EXAMPLE 11

The following dyeing composition is prepared:

| | |
|---|---|
| 2-Amino-3-nitro-5-methylaniline | 0.5 g |
| 3-Nitro-4-N-($\beta$-hydroxyethyl)-aminophenol | 0.15 g |
| Tetraaminoanthraquinone | 0.10 g |
| 2-Butoxyethanol | 10 g |
| Cemulsol NP$_4$ | 12 g |
| Cemulsol NP$_9$ | 15 g |
| Oxyethyleneated oleyl alcohol containing 2 mols of ethylene oxide (per mol of alcohol) | 1.5 g |
| Oxyethyleneated oleyl alcohol containing 4 mols of ethylene oxide | 1.5 g |
| Triethanolamine | 2 g |
| Water q.s.p. | 100 g |
| pH 9. | |

When applied for 35 minutes at 30° C. to hair which has been bleached straw blond, this mixture imparts to the hair, after rinsing and shampooing, a coppery medium chestnut colouration.

EXAMPLE 12

The following dyeing composition is prepared:

| | |
|---|---|
| 3-Nitro-ortho-phenylenediamine | 0.3 g |
| 3-Nitro-4-N'-methylamino-N,N-di-($\beta$-hydroxyethyl)-aniline | 0.11 g |
| N,N'-($\beta$-Hydroxyethyl)-nitro-para-phenylenediamine | 0.11 g |
| 96° strength alcohol | 10 g |
| Carboxymethylcellulose | 2 g |
| Ammonium lauryl-sulphate | 5 g |
| Monoethanolamine | 2 g |
| Water q.s.p. | 100 g |
| pH 10.5. | |

When applied for 25 minutes at 30° to hair which has been bleached straw blond, this mixture imparts to the hair, after rinsing and shampooing, a very coppery chestnut colouration.

EXAMPLE 13

The following dyeing composition is prepared:

| | |
|---|---|
| 2-N-Butylamino-3-nitro-5-methylaniline | 0.3 g |
| 3-Nitro-4-N'-methylamino-N,N-di-($\beta$-hydroxyethyl)-aniline | 0.05 g |
| 2-Butoxyethanol | 10 g |

-continued

| | |
|---|---|
| Diethanolamides of copra fatty acids | 2.2 g |
| Lauric acid | 0.8 g |
| Ethylene glycol monoethyl ether | 2 g |
| Monoethanolamine | 1 g |
| Water q.s.p. | 100 g |
| pH 8.5 | |

When applied for 30 minutes at 28° C. to hair which has been bleached white, this mixture imparts to the hair, after rinsing and shampooing, a light beige colouration with a golden sheen.

EXAMPLE 14

The following dyeing composition is prepared:

| | |
|---|---|
| 2-N-(β-Diethylaminoethyl)-amino-3-nitro-5-methylaniline | 1 g |
| 2-Butoxyethanol | 5 g |
| Lauryl alcohol containing 10.5 mols of ethylene oxide | 5 g |
| 22° B strength ammonia solution | 1 g |
| Water q.s.p. | 100 g |
| pH 9. | |

When applied to bleached hair for 25 minutes at 28° C., this dyeing composition imparts to the hair, after rinsing and shampooing, a colouration of 6.5 YR 5/10 on the Munsell scale.

EXAMPLE 15

The following dyeing composition is prepared:

| | |
|---|---|
| 2-N-(β-Hydroxypropyl)-amino-3-nitro-5-methylaniline hydrochloride | 0.5 g |
| Propylene glycol | 10 g |
| Carboxymethylcellulose | 10 g |
| Monoethanolamine | 5 g |
| Water q.s.p. | 100 g |

When applied for 25 minutes at 30° C. to hair which has been bleached white, this mixture imparts to the hair, after rinsing and shampooing, a colouration of 4 YR 7/7 on the Munsell scale.

EXAMPLE 16

The following dyeing composition is prepared:

| | |
|---|---|
| 2-N-(β,γ-dihydroxypropyl)-amino-3-nitro-5-methylaniline hydrochloride | 1.82 g |
| 3-Nitro-4-N-(β-hydroxyethyl)-aminophenol | 0.3 g |
| 3-Nitro-4-N'-methylamino-N,N-di-(β-hydroxyethyl)-aniline | 0.5 g |
| 2-Butoxyethanol | 10 g |
| Lauric acid monoethanolamide | 1.5 g |
| Lauric acid | 1 g |
| Hydroxyethylcellulose | 5 g |
| Monoethanolamine | 4 g |
| Water q.s.p. | 100 g |
| pH 10. | |

When applied to 90% naturally white hair for 25 minutes at 30° C., this mixture imparts a copper-red light chestnut colouration to the hair.

EXAMPLE 17

The following dyeing composition is prepared:

| | |
|---|---|
| 2-N-(β-Methoxyethyl)-amino-3-nitro-5-methylaniline | 0.6 g |
| 2-Butoxyethanol | 10 g |
| Carbopol 934 | 2 g |
| Monoethanolamine | 2 g |
| Water q.s.p. | 100 g |
| pH 8.8 | |

When applied to bleached hair for 30 minutes at 30° C., this dyeing composition imparts to the hair, after rinsing and shampooing, a colouration of 7.5 YR 7/6 on the Munsell scale.

EXAMPLE 18

The following dyeing composition is prepared:

| | |
|---|---|
| 2-N-(β-Hydroxypropyl)-amino-3-nitro-5-methylaniline hydrochloride | 1 g |
| Para-phenylenediamine | 0.25 g |
| Para-aminophenol | 0.065 g |
| Resorcinol | 0.2 g |
| Meta-aminophenol | 0.08 g |
| 2-Methyl-5-N-(β-Hydroxyethyl)-aminophenol | 0.05 g |
| 2-Butoxyethanol | 8 g |
| Carboxymethylcellulose | 2 g |
| Ammonium lauryl-sulphate | 5 g |
| Ammonium acetate | 1 g |
| Propylene glycol | 8 g |
| Masquol DTPA | 2 g |
| Thioglycolic acid | 0.4 g |
| 22° B strength ammonia solution | 10 g |
| Water q.s.p. | 100 g |
| pH 10.6. | |

100 g of hydrogen peroxide of 20 volumes strength are added at the time of use.

When applied for 30 minutes at 30° C. to hair which has been bleached straw blond, this mixture imparts to the hair, after rinsing and shampooing, a medium chestnut colouration with a coppery sheen.

EXAMPLE 19

The following dyeing composition is prepared:

| | |
|---|---|
| 2-Amino-3-nitro-5-methylaniline | 0.8 g |
| Para-phenylenediamine | 0.18 g |
| Para-aminophenol | 0.05 g |
| Resorcinol | 0.12 g |
| Meta-aminophenol | 0.115 g |
| 2,4-Diaminophenoxyethanol dihydrochloride | 0.03 g |
| Cemulsol NP4 | 12 g |
| Cemulsol NP9 | 15 g |
| Oleyl alcohol containing 2 mols of ethylene oxide | 1.5 g |
| Oleyl alcohol containing 4 mols of ethylene oxide | 1.5 g |
| Propylene glycol | 6 g |
| Trilon B | 0.12 g |
| 22° B strength ammonia solution | 11 g |
| Thioglycolic acid | 0.6 g |
| Water q.s.p. | 100 g |
| pH 10.5. | |

100 g of hydrogen peroxide of 20 volumes strength are added at the time of use.

When applied to 90% naturally white hair for 30 minutes at 30° C., this mixture imparts to the hair, after rinsing and shampooing, a coppery medium chestnut colouration.

EXAMPLE 20

The following dyeing composition is prepared:

| | |
|---|---|
| 2-N-(β-Diethylaminoethyl)-amino-3-nitro-5-methylaniline | 1.5 g |
| 3-Nitro-4-N'-methylamino-N,N-di-(β-hydroxyethyl)-aniline | 0.2 g |
| 2-Butoxyethanol | 10 g |
| Carboxymethylcellulose | 10 g |
| Monoethanolamine | 5 g |
| Water q.s.p. | 100 g |
| pH 10. | |

When applied for 30 minutes at 30° C. to hair which has been bleached white, this mixture imparts to the hair, after rinsing and shampooing, an ashen beige colouration.

EXAMPLE 21

The following dyeing composition is prepared:

| | |
|---|---|
| 2-N-(β-Hydroxyethyl)-amino-3-nitro-5-methyl-aniline | 1.2 g |
| 2-Butoxyethanol | 10 g |
| Lauric acid monoethanolamide | 1.5 g |
| Lauric acid | 1 g |
| Hydroxyethylcellulose | 5 g |
| Monoethanolamine | 2 g |
| Water q.s.p. | 100 g |
| pH 10. | |

When applied for 25 minutes at 28° C. to hair which has been bleached white, this mixture imparts to the hair, after rinsing and shampooing, a colouration of 5 YR 8/6 on the Munsell scale.

EXAMPLE 22

The following dyeing composition is prepared:

| | |
|---|---|
| 2-N-(β-Hydroxyethyl)-amino-3-nitro-5-methylaniline | 1.21 g |
| Para-phenylenediamine | 0.5 g |
| Resorcinol | 0.1 g |
| Meta-aminophenol | 0.21 g |
| Ortho-aminophenol | 0.17 g |
| Carbopol 934 | 1.5 g |
| 96° strength alcohol | 11 g |
| 2-Butoxyethanol | 5 g |
| Trimethylcetylammonium bromide | 1 g |
| Trilon B | 0.1 g |
| 22° B strength ammonia solution | 10 g |
| Thioglycolic acid | 0.2 g |
| Water q.s.p. | 100 g |
| pH 10.5. | |

100 g of hydrogen peroxide of 20 volumes strength are added at the time of use.

When applied to 90% naturally white hair for 25 minutes at 28° C., this mixture imparts to the hair, after rinsing and shampooing, a deep chestnut colouration with a coppery sheen.

EXAMPLE 23

The following dyeing composition is prepared:

| | |
|---|---|
| 3-Nitro-ortho-phenylenediamine | 0.5 g |
| 2-Methyl-6-nitroaniline | 0.2 g |
| Para-phenylenediamine | 0.08 g |
| 2-Methylresorcinol | 0.045 g |
| Meta-aminophenol | 0.06 g |
| Cemulsol NP4 | 21 g |
| Cemulsol NP9 | 24 g |
| Oleic acid | 4 g |
| 2-Butoxyethanol | 3 g |
| 96° strength ethanol | 10 g |
| Masquol DTPA | 2.5 g |
| 35° B strength sodium bisulphite solution | 1 g |
| 22° B strength ammonia solution | 10 g |
| Water q.s.p. | 100 g |
| pH 11. | |

80 g of hydrogen peroxide of 20 volumes strength are added at the time of use.

When applied to 90% naturally white hair for 25 minutes at 30° C., this mixture imparts to the hair, after rinsing and shampooing, a very golden deep blond colouration.

The following Examples illustrate the preparation of the new compounds used according to the invention.

PREPARATION EXAMPLE 1

Preparation of 2-N-butylamino-3-nitro-5-methylaniline

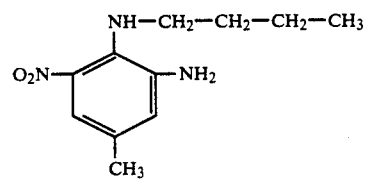

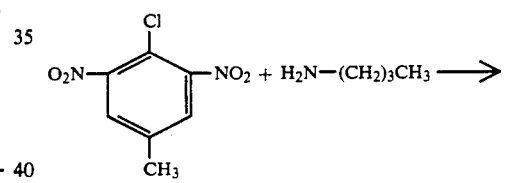

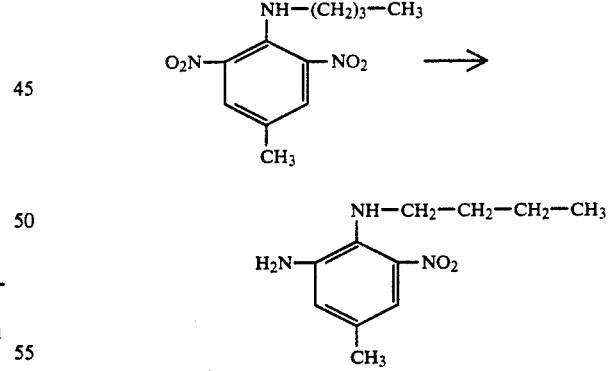

a) Preparation of 2,6-dinitro-4-methyl-N-butylaniline 0.05 mol (10.8 g) of 2,6-dinitro-4-methylchlorobenzene is added gradually, in the course of 10 minutes, whilst stirring, to 25 ml of butylamine, the reaction medium being cooled as necessary so as not to exceed 50° C. When the addition has ended, stirring is maintained for 5 minutes and the reaction medium is then poured into 100 ml of iced water. The expected product precipitates and is filtered off, washed with water and recrystallised from ethanol. After drying in vacuo, it melts at 52° C.

| Analysis | Calculated for $C_{11}H_{15}N_3O_4$ | Found |
|---|---|---|
| C% | 52.17 | 52.13 |
| H% | 5.93 | 6.04 |
| N% | 16.60 | 16.59 |
| O% | 25.30 | 25.34 | b) Preparation of 2-N-butylamino-3-nitro-5-methylaniline 0.041 mol (10.4 g) of 2,6-dinitro-4-methyl-N-butylaniline is added to 50 ml of ethanol to which 10.8 g of cyclohexene and 2.8 g of 10% strength Pd-on-C have been added. The reaction medium is heated under reflux for one hour and then filtered hot in order to remove the catalyst. The filtrate is cooled to −15° C. The expected product crystallises. It is filtered off, washed with a small amount of iced alcohol and dried in vacuo. It melts at 68° C.

| Analysis | Calculated for $C_{11}H_{17}N_3O_2$ | Found |
|---|---|---|
| C% | 59.19 | 59.33 |
| H% | 7.62 | 7.75 |
| N% | 18.83 | 18.98 |
| O% | 14.35 | 14.44 |

PREPARATION EXAMPLE 2

Preparation of 2-N-(β-methoxyethyl)-amino-3-nitro-5-methylaniline

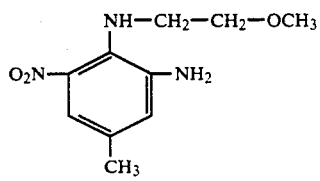

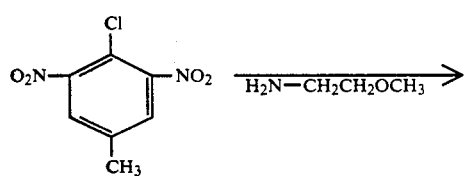

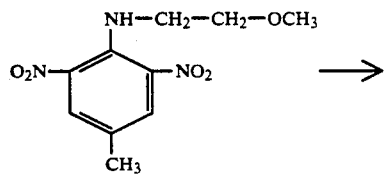

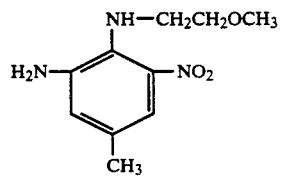

a) Preparation of 2,6-dinitro-4-methyl-N-(β-methoxyethyl)aniline 0.05 mol (10.8 g) of 2,6-dinitro-4-methylchlorobenzene is added gradually, in the course of 10 minutes, whilst stirring, to 25 ml of methoxyethylamine, the reaction medium being cooled as necessary so as not to exceed 50° C. When the addition has ended, the stirring is maintained for 5 minutes and the reaction medium is then poured into 100 ml of iced water. The expected product precipitates. It is filtered off, washed with water and recrystallised from ethanol. After drying in vacuo, it melts at 75° C.

| Analysis | Calculated for $C_{10}H_{13}N_3O_5$ | Found |
|---|---|---|
| C% | 47.06 | 47.08 |
| H% | 5.13 | 4.99 |
| O% | 31.34 | 31.07 |
| N% | 16.47 | 16.50 | b) Preparation of 2-N-methoxyethylamino-3-nitro-5-methylaniline 0.03 mol (7.65 g) of 2,6-dinitro-4-methyl-N-(β-methoxyethyl)-aniline is dissolved in 38 ml of absolute alcohol containing 12.3 g of cyclohexene and 3.8 g of 10% strength Pd-on-C. The alcoholic solution is then heated under reflux for 15 minutes. The reaction medium is filtered hot in order to remove the catalyst, and then, after cooling, 15 ml of alcohol saturated with hydrogen chloride are added. The expected product precipitates in the form of the hydrochloride. The hydrochloride is filtered off, washed with a small amount of alcohol and then redissolved in water. This aqueous solution is rendered alkaline with the aid of ammonia solution in order to precipitate the expected product, which is filtered off, washed with water and recrystallised from ethanol; it melts at 71° C.

| Analysis | Calculated for $C_{10}H_{15}N_3O_3$ | Found |
|---|---|---|
| C% | 53.33 | 53.46 |
| H% | 6.67 | 6.70 |
| N% | 18.67 | 18.55 |
| O% | 21.33 | 21.27 |

PREPARATION EXAMPLE 3

Preparation of 2-nitro-4-methyl-6-amino-4'-hydroxydiphenylamine

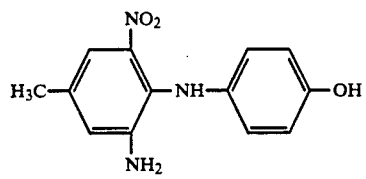

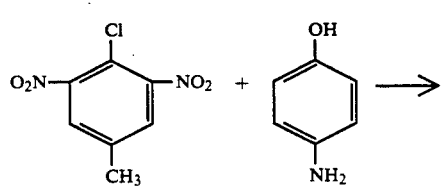

-continued

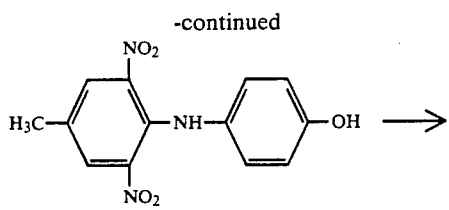

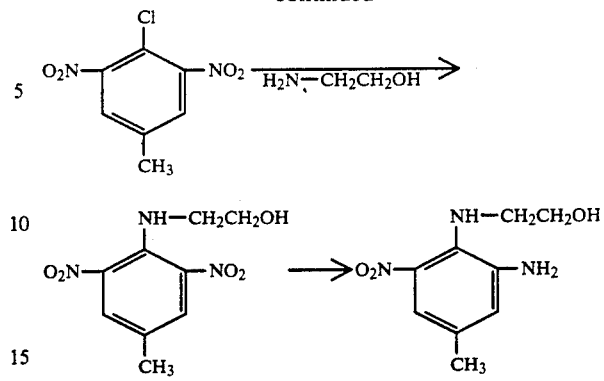

a) Preparation of 2,6-dinitro-4-methyl-4'-hydroxydiphenylamine 0.1 mol (10.9 g) of para-aminophenol and 0.05 mol (10.83 g) of 2,6-dinitro-4-methylchlorobenzene in 60 ml of alcohol are heated under reflux for 2 hours. After the reaction medium has cooled, the insoluble 2,6-dinitro-4-methyl-4'-hydroxydiphenylamine is filtered off and washed with alcohol. After recrystallisation from alcohol and drying in vacuo, the product melts at 192° C.

b) Preparation of 2-nitro-4-methyl-6-amino-4'-hydroxydiphenylamine 0.038 mol (11 g) of 2,6-dinitro-4-methyl-4'-hydroxydiphenylamine is added to 200 ml of alcohol to which 20 ml of 22° B strength ammonia solution has been added, and hydrogen sulphide is then bubbled into this solution for 30 minutes. The reaction medium is then heated under reflux for 2 hours. The alcoholic solution is filtered after cooling and the filtrate is then evaporated to dryness in vacuo. The residue is taken up in 150 ml of 2N hydrochloric acid solution. The insoluble material is removed by filtration and the filtrate is then rendered alkaline with the aid of ammonia solution. The expected product precipitates. It is filtered off, washed with water and then recrystallised from ethanol; it melts at 163° C.

| Analysis | Calculated for $C_{13}H_{13}N_3O_3$ | Found |
|---|---|---|
| C% | 60.23 | 60.03 |
| H% | 5.02 | 5.11 |
| N% | 16.22 | 16.25 |
| O% | 18.53 | 18.55 |

PREPARATION EXAMPLE 4

Preparation of 2-N-(β-hydroxyethyl)-amino-3-nitro-5-methylaniline

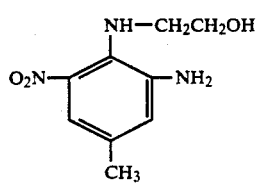

a) Preparation of 2,6-dinitro-4-methyl-N-(β-hydroxyethyl)aniline 0.35 mol (76 g) of 2,6-dinitro-4-methylchlorobenzene is added gradually, in the course of 10 minutes, whilst stirring, to 150 ml of ethanolamine, the reaction medium being cooled as necessary so as not to exceed 75° C. When the addition has ended, the stirring is maintained for 5 minutes and the reaction medium is then poured into 600 g of iced water. The expected product precipitates. It is filtered off, washed with water and then recrystallised from ethanol. After drying in vacuo, it melts at 131° C.

| Analysis | Calculated for $C_9H_{11}N_3O_5$ | Found |
|---|---|---|
| C% | 44.81 | 44.93 |
| H% | 4.56 | 4.49 |
| N% | 17.43 | 17.32 |
| O% | 33.20 | 33.00 | b) Preparation of 2-N-(β-hydroxyethyl)-amino-3-nitro-5-methylaniline 0.4 mol (96.4 g) of 2,6-dinitro-4-methyl-N-(β-hydroxyethyl)-aniline is added to 1,500 ml of absolute alcohol to which 160 ml of 22° B strength ammonia solution have been added, and hydrogen sulphide is then bubbled into this alcoholic solution for 30 minutes. The temperature rises to 50° C. and then drops again. The bubbling is then stopped and the reaction medium is subsequently heated under reflux for one hour. After concentration of the alcoholic solution to 300 ml, the inorganic salts are filtered off. The filtrate is then evaporated to dryness. The residue obtained in the form of a red oil is redissolved in 80 ml of 96° strength ethanol. After the addition of 170 ml of an ethanolic solution of hydrogen chloride (containing 7 mols of hydrogen chloride per liter of alcohol) and cooling to 0° C., the expected product, which has precipitated in the form of the hydrochloride, is filtered off. After washing with alcohol, this hydrochloride is dissolved in 300 ml of water. On neutralisation of this solution with the aid of ammonia solution, 2-N-(β-hydroxyethyl)-amino-3-nitro-5-methylaniline is precipitated. This product is filtered off, washed with water and then recrystallised from 96° strength alcohol. After drying in vacuo, it melts at 96° C.

| Analysis | Calculated for $C_9H_{13}N_3O_3$ | Found |
|---|---|---|
| C% | 51.18 | 51.09 |

-continued

| Analysis | Calculated for C9H13N3O3 | Found |
|---|---|---|
| H% | 6.16 | 6.21 |
| N% | 19.91 | 20.06 |
| O% | 22.75 | 22.79 |

PREPARATION EXAMPLE 5

Preparation of
2-amino-3-nitro-5-methyl-N-(β-hydroxyethyl)aniline

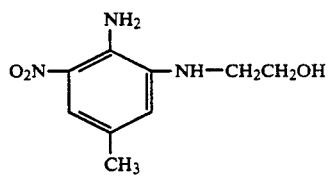

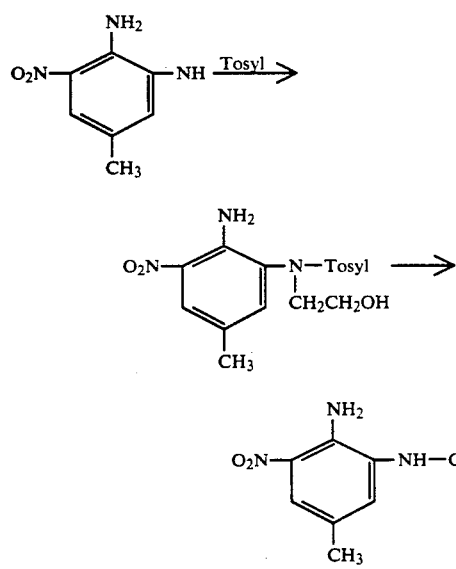

a) Preparation of 2-amino-3-nitro-5-methyl-N-(β-hydroxyethyl)-N-tosylaniline 0.087 mol (28 g) of 2-amino-3-nitro-5-methyl-N-tosylaniline is dissolved in 85 ml of DMF heated beforehand on a boiling water-bath. 9.7 g of quicklime are then added and 0.174 mol (21.75 g) of glycol bromohydrin is then introduced gradually, in the course of 30 minutes and whilst stirring, the heating on the boiling water-bath being maintained. After 1½ hours, the reaction medium is filtered hot and the filtrate is then poured into 250 ml of iced water. The expected product precipitates. It is filtered off, washed with water and dried in vacuo. After recrystallisation from acetic acid and drying in vacuo, it melts at 201° C.

| Analysis | Calculated for C16H19N3O5S | Found |
|---|---|---|
| C% | 52.60 | 52.47 |
| H% | 5.21 | 5.14 |
| N% | 11.51 | 11.41 |
| O% | 21.92 | 21.81 |
| S% | 8.77 | 8.68 | b) Preparation of 2-amino-3-nitro-5-methyl-N-(β-hydroxyethyl)-aniline 0.0458 mol (16.7 g) of 2-amino-3-nitro-5-methyl-N-(β-hydroxyethyl)-N-tosylaniline is introduced, whilst stirring, into 167 ml of concentrated sulphuric acid to which 48 ml of water has been added. The mixture is heated for 1 hour on a boiling water-bath and then poured onto 850 g of crushed ice. The sulphuric acid solution is neutralised with the aid of ammonia solution. The expected product precipitates. After filtration, washing with water, drying in vacuo and recrystallisation from ethanol, it melts at 166° C.

| Analysis | Calculated for C9H13O3N3 | Found |
|---|---|---|
| C% | 51.18 | 50.93 |
| H% | 6.16 | 6.20 |
| N% | 19.91 | 19.85 |
| O% | 22.75 | 22.68 |

PREPARATION EXAMPLE 6

Preparation of
2-amino-3-nitro-5-methyl-N-methylaniline

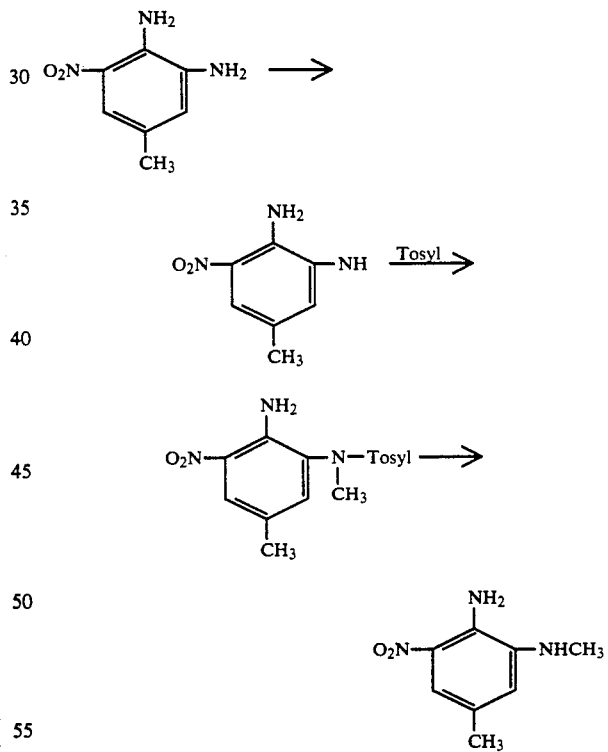

a) Preparation of 2-amino-3-nitro-5-methyl-N-tosylaniline 0.15 mol (25.05 g) of 2-amino-3-nitro-5-methylaniline is dissolved in 75 ml of pyridine, and 0.165 mol (31.4 g) of para-toluenesulphonyl chloride is then added gradually, whilst stirring, at between 40° and 45° C. When the addition has ended, the stirring is maintained for 1 hour at 45° C., the reaction medium is then poured into 450 ml of iced water and ther pyridine is neutralised with the aid of hydrochloric acid. The expected product which has precipitated is filtered off, washed with water and then recrystallised from acetic acid. After drying in vacuo, it melts at 184° C.

| Analysis | Calculated for $C_{14}H_{15}N_3O_4S$ | Found |
|---|---|---|
| C% | 52.34 | 52.33 |
| H% | 4.67 | 4.69 |
| N% | 13.08 | 12.89 |
| O% | 19.94 | 19.86 |
| S% | 9.97 | 10.12 | b) Preparation of 2-amino-3-nitro-5-methyl-N-methyl-N-tosylaniline 0.246 mol (79 g) of 2-amino-3-nitro-5-methyl-N-tosylaniline is dissolved in 260 ml of normal sodium hydroxide solution at 40° C. 0.286 mol (30 ml) of methyl sulphate is added gradually in the course of 3 hours, the temperature being kept at about 40° C. Towards the end of the addition of the methyl sulphate, the pH of the reaction medium is kept alkaline by simultaneously adding 20 ml of normal sodium hydroxide solution. After cooling to about 10° C., the expected product which has precipitated is filtered off. It is washed with a normal sodium hydroxide solution and then with water and recrystallised from acetic acid. After drying in vacuo, it melts at 208° C.

| Analysis | Calculated for $C_{15}H_{17}N_3O_4S$ | Found |
|---|---|---|
| C% | 53.73 | 53.81 |
| H% | 5.07 | 5.11 |
| N% | 12.54 | 12.39 |
| O% | 19.10 | 19.01 |
| S% | 9.55 | 9.41 | c) Preparation of 2-amino-3-nitro-5-methyl-N-methylaniline 0.1785 mol (59.8 g) of 2-amino-3-nitro-N-methyl-N-tosylaniline is added gradually, in the course of 1 hour 15 minutes, whilst stirring, to 354 ml of concentrated sulphuric acid to which 60 ml of water has been added and which has been heated to 90° C. beforehand. The heating is maintained for a further 15 minutes and the reaction medium is then poured into 1.5 kg of iced water. The expected product precipitates in the form of the sulphate. It is filtered off and washed with a small amount of iced water. The sulphate is suspended in water and, on adding ammonia solution, whilst stirring, 2-amino-3-nitro-5-methyl-N-methylaniline is freed; after filtration, washing with water and drying in vacuo, it melts at 113° C.

| Analysis | Calculated for $C_8H_{11}N_3O_2$ | Found |
|---|---|---|
| C% | 53.04 | 53.12 |
| H% | 6.08 | 6.13 |
| N% | 23.20 | 23.14 |
| O% | 17.68 | 17.54 |

PREPARATION EXAMPLE 7

Preparation of 2-amino-3-nitro-N-methylaniline

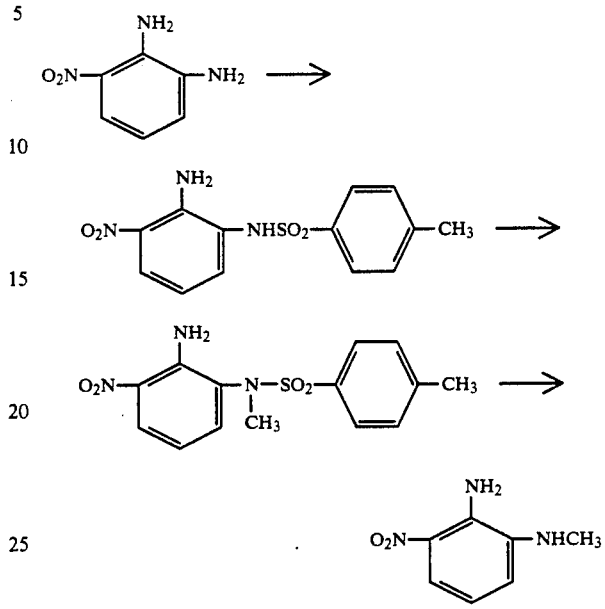

a) Preparation of 2-amino-3-nitro-N-tosylaniline 0.1 mol (15.3 g) of 3-nitro-ortho-phenylenediamine is dissolved in 50 ml of pyridine, and 0.11 mol (21 g) of para-toluenesulphonyl chloride is then added gradually, whilst stirring, at between 40° and 45° C. When the addition has ended, the stirring is maintained for 15 minutes and the reaction medium is then poured into 250 ml of iced water. The expected product precipitates. It is filtered off, washed with water and recrystallised from acetic acid. It melts at 195° C.

b) Preparation of 2-amino-3-nitro-N-methyl-N-tosylaniline 0.093 mol (28.5 g) of 2-amino-3-nitro-N-tosylaniline is dissolved in 112 ml of normal sodium hydroxide solution at 30° C. 0.122 mol (15.45 g) of methyl sulphate is added gradually, in the course of 1 hour 30 minutes, whilst stirring. The temperature remains between 35° and 40° C. Towards the end of the addition of the methyl sulphate, 3 ml of 10N sodium hydroxide solution are gradually added simultaneously in order to keep the pH alkaline.

The reaction medium is cooled and the expected product which has precipitated is then filtered off. It is washed with a normal sodium hydroxide solution and then with water and alcohol. After recrystallization from acetic acid and drying in vacuo, it melts at 183° C.

c) Preparation of 2-amino-3-nitro-N-methylaniline 0.0716 mol (23 g) of 2-amino-3-nitro-N-methyl-N-tosylaniline is added gradually, in the course of 10 minutes whilst stirring, to 230 ml of concentrated sulphuric acid to which 23 ml of water has been added and which has been heated to 90° C. beforehand. When the addition has ended, the reaction medium is kept at 90° C. for 5 minutes and then poured onto crushed ice. The acid aqueous solution obtained is rendered alkaline with the aid of ammonia solution in order to precipitate the expected product. The latter is filtered off, washed with water and recrystallised from 40 ml of alcohol. After drying in vacuo, it melts at 93° C.

| Analysis | Calculated for C₇H₉N₃O₂ | Found |
|---|---|---|
| C% | 50.30 | 50.51 |
| H% | 5.39 | 5.31 |
| N% | 25.15 | 25.04 |
| O% | 19.16 | 19.02 |

PREPARATION EXAMPLE 8

Preparation of
2-N-(β-hydroxypropyl)-amino-3-nitro-5-methylaniline hydrochloride

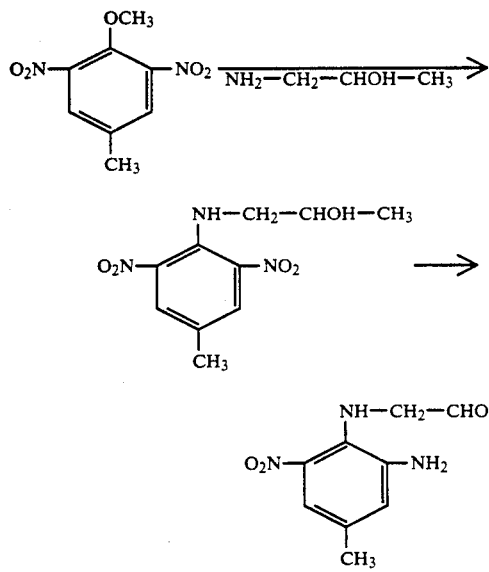

a) Preparation of 2,6-dinitro-4-methyl-N-(β-hydroxypropyl)-aniline 0.05 mol (10.6 g) of 2,6-dinitro-4-methylanisole is introduced gradually, whilst stirring, into 30 ml of 1-aminopropan-2-ol. The reaction medium is heated at 60° C. for 30 minutes and then poured into 120 g of iced water. The expected product precipitates. It is filtered off, washed with water and then recrystallised from an aqueous-alcoholic mixture. After drying in vacuo, it melts at 80° C.

| Analysis | Calculated for C₁₀H₁₃N₃O₅ | Found |
|---|---|---|
| C% | 47.06 | 47.05 |
| H% | 5.13 | 5.10 |
| O% | 31.34 | 31.44 |
| N% | 16.47 | 16.36 | b) Preparation of 2-N-(β-hydroxypropyl)-amino-3-nitro-5-methylaniline hydrochloride 0.02 mol (5.10 g) of 2,6-dinitro-4-methyl-N-(β-hydroxypropyl)-aniline is dissolved in 40 ml of absolute alcohol containing 0.1 mol (8.6 g) of cyclohexene. 2.5 g of 10% strength Pd-on-C are added and the alcoholic solution is then heated under reflux for 10 minutes. After cooling, the reaction medium is filtered in order to remove the catalyst. About 20 ml of alcohol are driven off in vacuo and 7 ml of ethanol saturated with hydrogen chloride are then added. After cooling to −10° C., the expected product crystallises. It is filtered off, washed with a small amount of alcohol and then recrystallised from absolute alcohol. After drying in vacuo, the expected hydrochloride melts at between 145° and 150° C. with decomposition.

| Analysis | Calculated for C₁₀H₁₅N₃O₃.HCl | Found |
|---|---|---|
| C% | 45.89 | 45.96 |
| H% | 6.12 | 6.14 |
| N% | 16.06 | 16.19 |
| O% | 18.36 | 18.43 |
| Cl% | 13.58 | 13.76 |

PREPARATION EXAMPLE 9

Preparation of
2-N-(β,γ-dihydroxypropyl)-amino-3-nitro-5-methylaniline hydrochloride

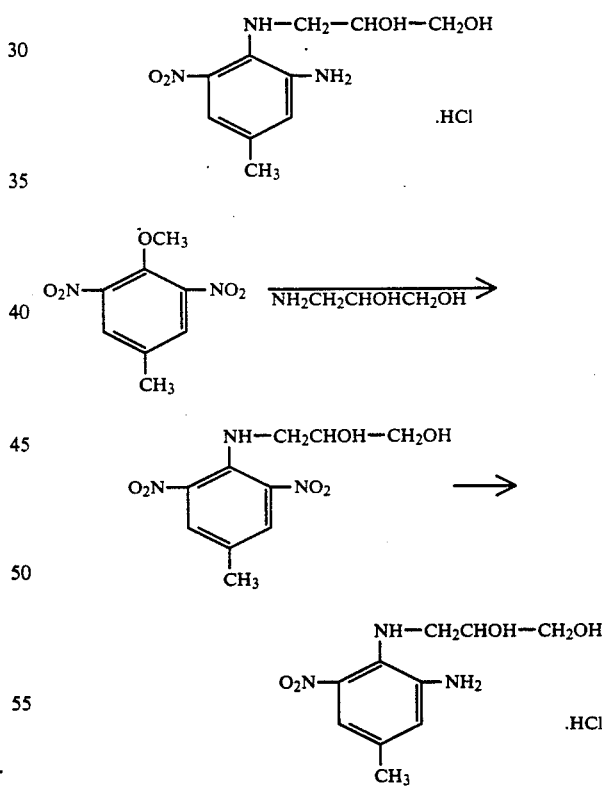

a) Preparation of 2,6-dinitro-4-methyl-N-(β,γ-dihydroxypropyl)-aniline 0.05 mol (10.6 g) of 2,6-dinitro-4-methylanisole is dissolved in 50 ml of absolute alcohol. 0.1 mol (9.1 g) of 1-aminopropane-2,3-diol is added gradually to this solution, whilst stirring. The solution is heated under reflux for 3 hours 30 minutes. The alcohol is driven off in vacuo and 40 ml of iced water are added to the residual red oil. The expected product crystallises. It is filtered off and washed with water. After recrystallisation from an aqueous-alcoholic mixture and drying in vacuo, it melts at 118° C.

| Analysis | Calculated for $C_{10}H_{13}N_3O_6$ | Found |
|---|---|---|
| C% | 44.28 | 44.33 |
| H% | 4.80 | 4.80 |
| N% | 15.50 | 15.72 |
| O% | 35.42 | 35.80 | b) Preparation of 2-N-($\beta,\gamma$-dihydroxypropyl)-amino-3-nitro-5-methylaniline hydrochloride 0.03 mol (8.13 g) of 2,6-dinitro-4-methyl-N-($\beta,\gamma$-dihydroxypropyl)-aniline is dissolved in 60 ml of absolute alcohol containing 12.3 g of cyclohexene. 4 g of 10% strength Pd-on-C are added. The alcoholic solution is heated under reflux for 10 minutes. After cooling, the reaction medium is filtered in order to remove the catalyst. About 30 ml of alcohol are driven off in vacuo and 8 ml of ethanol saturated with hydrogen chloride are then added. After cooling to $-10°$ C., the expected product precipitates. The hydrochloride is filtered off, washed with a small amount of ethyl ether and dried in vacuo. After two recrystallisations from absolute alcohol, the expected product melts at between 130° and 134° C. with decomposition.

| Analysis | Calculated for $C_{10}H_{15}N_3O_4 \cdot HCl$ | Found |
|---|---|---|
| C% | 43.24 | 43.18 |
| H% | 5.77 | 5.82 |
| N% | 15.14 | 15.30 |
| O% | 23.06 | 23.10 |
| Cl% | 12.79 | 12.88 |

PREPARATION EXAMPLE 10

Preparation of 2-N-methylamino-3-nitro-5-methylaniline

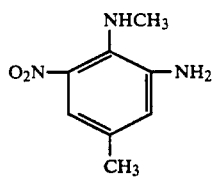

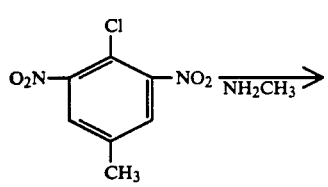

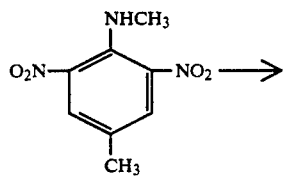

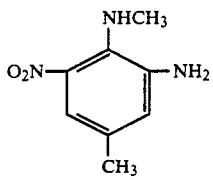

a) Preparation of 2,6-dinitro-4-methyl-N-methylaniline 0.05 mol (18 g) of 2,6-dinitro-4-methylchlorobenzene is added gradually, whilst stirring, to 40 ml of a 33% strength solution of methylamine in ethanol. The temperature rises to 50° C. and the expected derivative precipitates immediately. When the addition has ended, the stirring is maintained for 5 minutes and the 2,6-dinitro-4-methyl-N-methylaniline is then filtered off and washed with water; after recrystallisation from alcohol and drying in vacuo, it melts at 132° C.

| Analysis | Calculated for $C_8H_9N_3O_4$ | Found |
|---|---|---|
| C% | 45.50 | 45.40 |
| H% | 4.27 | 4.38 |
| N% | 19.91 | 19.94 |
| O% | 30.33 | 30.26 | b) Preparation of 2-N-methylamino-3-nitro-5-methylaniline 0.0407 mol (8.6 g) of 2,6-dinitro-4-methyl-N-methylaniline is dissolved in 45 ml of alcohol containing 0.203 mol (16.7 g) of cyclohexene. 4.3 g of 10% strength Pd-on-C are added. The mixture is heated under reflux for 20 minutes and the boiling reaction medium is then filtered in order to remove the catalyst. The expected product crystallises on cooling of the filtrate. It is filtered off, washed with a small amount of alcohol and recrystallised from ethanol. After drying in vacuo, it melts at 131° C.

| Analysis | Calculated for $C_8H_{11}N_3O_2$ | Found |
|---|---|---|
| C% | 53.04 | 53.07 |
| H% | 6.08 | 6.06 |
| N% | 23.20 | 23.26 |
| O% | 17.68 | 17.57 |

PREPARATION EXAMPLE 11

Preparation of 2-N-($\beta$-diethylaminoethyl)-amino-3-nitro-5-methylaniline

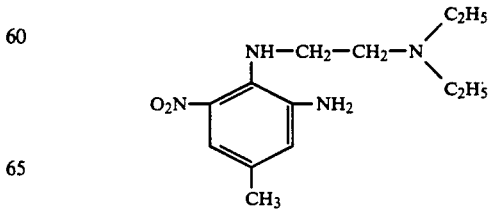

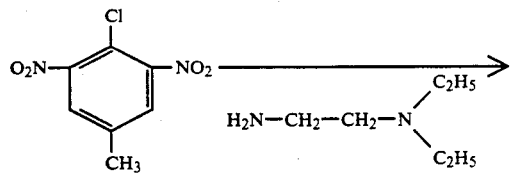

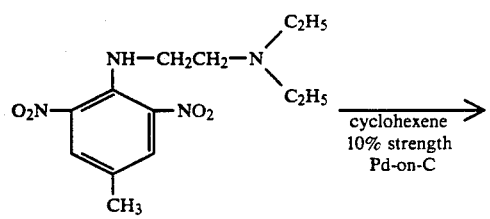

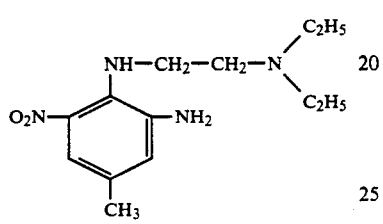

a) Preparation of 2,6-dinitro-4-methyl-N,N-diethylaminoethylaniline 0.05 mol (10.8 g) of 2,6-dinitro-4-methylchlorobenzene is added gradually, in the course of 10 minutes, whilst stirring, to 25 ml of N,N-diethylaminoethylamine, the reaction medium being cooled so as not to exceed 50° C. When the addition has ended, the stirring is maintained for 5 minutes and the reaction medium is then poured into 150 ml of iced water. The expected product precipitates. It is filtered off, washed with water and recrystallised from ethanol. After drying in vacuo, it melts at 72° C.

| Analysis | Calculated for $C_{13}H_{20}N_4O_4$ | Found |
|---|---|---|
| C% | 52.70 | 52.59 |
| H% | 6.76 | 6.79 |
| N% | 18.92 | 18.99 |
| O% | 21.62 | 21.50 | b) Preparation of 2-N-($\beta$-diethylaminoethyl)-amino-3-nitro-5-methylaniline 0.03 mol (8.52 g) of 2,6-dinitro-4-methyl-N,N-diethylaminoethylaniline is dissolved in 42 ml of ethanol containing 0.15 mol (12.3 g) of cyclohexene and 4.3 g of 10% strength Pd-on-C. The reaction mixture is heated under reflux for 30 minutes and is then filtered at the boil in order to remove the catalyst. After cooling, 30 ml of a solution of hydrogen chloride in ethanol (containing 7 mols of hydrogen chloride per liter) are added to the filtrate. The expected product precipitates in the form of the hydrochloride. The hydrochloride is filtered off, washed with a small amount of acetone and then dissolved in 30 ml of water. On neutralisation of this aqueous solution with the aid of ammonia solution, 2-N-($\beta$-diethylaminoethyl)-amino-3-nitro-5-methylaniline is precipitated. This product is filtered off, washed with water and then recrystallised from 95° strength alcohol. After drying in vacuo, it melts at 45° C.

| Analysis | Calculated for $C_{13}H_{22}N_4O_2$ | Found |
|---|---|---|
| C% | 58.65 | 58.75 |
| H% | 8.27 | 8.29 |
| N% | 21.05 | 21.03 |
| O% | 12.03 | 11.92 |

PREPARATION EXAMPLE 12

Preparation of 2-N-($\beta$-hydroxyethyl)-amino-3-nitroaniline

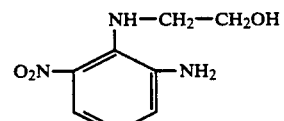

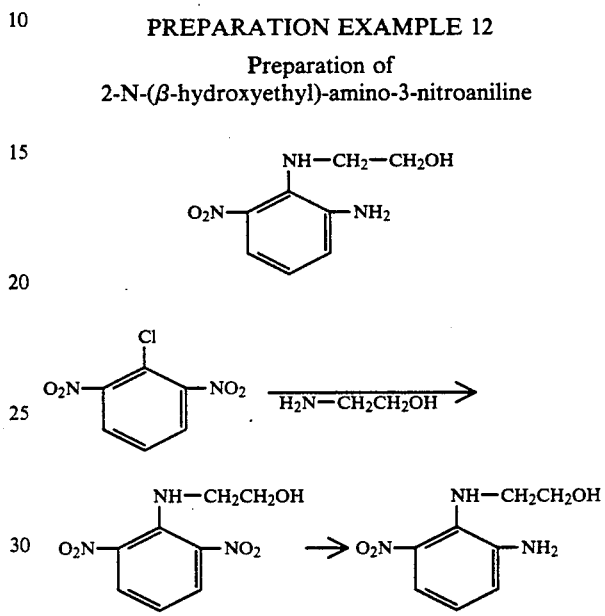

a) Preparation of 2,6-dinitro-N-($\beta$-hydroxyethyl)-aniline 0.05 mol (10.125 g) of 2,6-dinitrochlorobenzene is added gradually, whilst stirring, to 25 ml of ethanolamine, the reaction medium being cooled so that the temperature does not exceed 50° C. The reaction medium is poured into 100 ml of iced water. The expected product precipitates. It is filtered off, washed with water and recrystallised from ethanol. After drying in vacuo, it melts at 100° C.

| Analysis | Calculated for $C_8H_9N_3O_5$ | Found |
|---|---|---|
| C% | 42.29 | 42.36 |
| H% | 3.96 | 4.05 |
| N% | 18.50 | 18.44 |
| O% | 35.24 | 35.30 | b) Preparation of 2-N-($\beta$-hydroxyethyl)-amino-3-nitroaniline 0.04 mol (9.1 g) of 2,6-dinitro-N-($\beta$-hydroxyethyl)aniline is added to 160 ml of absolute ethanol to which 16 ml of 22° B strength ammonia solution have been added, and hydrogen sulphide is then bubbled into this alcoholic solution for 30 minutes. The bubbling is stopped and the reaction medium is then heated under reflux for 2 hours. The boiling alcoholic solution is filtered in order to remove the inorganic salts, and the filtrate is then evaporated to dryness. The red residue obtained is redissolved in hot alcohol. On cooling, the expected product crystallises. It is filtered off, washed with a small amount of cold alcohol and dried in vacuo. It melts at 78° C.

| Analysis | Calculated for $C_8H_{11}N_3O_3$ | Found |
|---|---|---|
| C% | 48.73 | 48.88 |
| H% | 5.58 | 5.61 |
| N% | 21.32 | 21.46 |
| O% | 24.37 | 24.49 |

The various tradenames used in the foregoing examples are explained in greater detail below:

CARBOPOL 934: Acrylic acid polymer having a molecular weight of 2 to 3 million, sold by Goodrich Chemical Company.

CEMULSOL NP$_4$: Nonylphenol containing 4 mols of ethylene oxide, sold by Rhône Poulenc.

CEMULSOL NP$_9$: Nonylphenol containing 9 mols of ethylene oxide, sold by Rhône Poulenc.

ALFOL C$_{16}$/$_{18}$ (50/50): Cetyl/stearyl alcohol sold by Condéa.

Lanette wax E: Partially sulphated cetyl/stearyl alcohol sold by Henkel.

CEMULSOL B: Oxyethyleneated castor oil sold by Rhône Poulenc.

MASQUOL DTPA: Sodium salt of diethylenetriaminepentaacetic acid.

TRILON B: Sodium salt of ethylenediaminetetraacetic acid.

We claim:

1. A composition suitable for dyeing keratin fibres, which comprises, in an amount effective for dyeing said keratin fibres, at least one dyestuff corresponding to the formula (I)

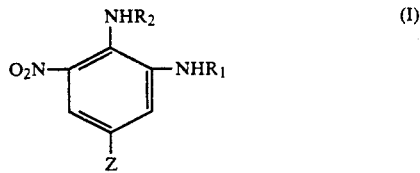

in which R$_1$ is a hydrogen atom, R$_2$ is a monohydroxyalkyl or polyhydroxyalkyl group, and Z denotes a hydrogen atom or an alkyl group, or a cosmetically acceptable salt thereof, wherein each of said alkyl groups contains 1–4 carbon atoms.

2. A composition according to claim 1 in which Z denotes hydrogen or methyl and R$_2$ denotes β-hydroxyethyl, β-hydroxypropyl or β-γ-dihydroxypropyl.

3. A composition according to claim 1 in which Z denotes methyl.

4. A composition according to claim 1 which comprises a solvent selected from water, a lower alkanol, a glycerol, glycol or glycol ether, or a mixture of two or more thereof.

5. A composition according to claim 1 which also contains at least one of a surface active agent, thickener, penetrating agent, sequestering agent, film-forming agent, buffer, perfume or alkalizing or acidifying agent.

6. A composition according to claim 1 which has a pH of 3 to 11.5.

7. A composition according to claim 6 which has a pH of 5 to 11.5.

8. A composition according to claim 1 intended to be used for direct coloration of the hair which also contains at least one dyestuff which is an azo or anthraquinone dyestuff or a nitrobenzene dyestuff other than of the formula (I).

9. A composition according to claim 1 intended for use as a wavesetting lotion which is in the form of an aqueous, alcoholic or aqueous-alcoholic solution containing at least one cosmetic resin.

10. A composition according to claim 1 intended to be used for oxidation dyeing, which contains at least one oxidation dyestuff precursor.

11. A composition according to claim 10 which has a pH of 7 to 11.5 which also contains a reducing agent.

12. A composition according to claim 1 which has an amount from 0.001 to 5% by weight of said at least one dyestuff corresponding to the formula (I).

13. Process for the coloration of keratin fibres which comprises applying thereto a composition as defined in claim 1, leaving it on the fibres for 5 to 70 minutes and rinsing the fibres, optionally washing and rinsing them again, and drying them.

14. Process for the coloration of keratin fibres, which comprises applying to washed and rinsed fibres a composition as defined in claim 9, optionally winding the fibres onto rollers and drying them.

15. Process for the coloration of keratin fibres which comprises applying thereto a composition as defined in claim 10 to which an oxidizing agent has optionally been added, leaving it on the fibres for 10 to 50 minutes and rinsing the fibres, optionally shampooing and rinsing them again, and drying them.

16. A composition suitable for dyeing human hair which comprises an amount from 0.001 to 5% by weight of at least one dyestuff corresponding to the formula (I):

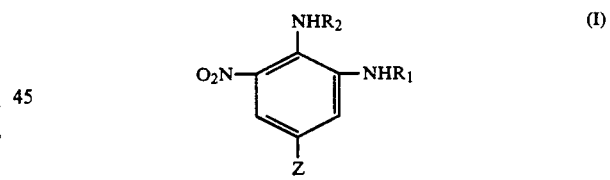

in which R$_1$ and R$_2$ independently of one another denote a hydrogen atom, an alkyl group, a monohydroxyalkyl or polyhydroxyalkyl group, an alkoxy alkyl group, or an aminoalkyl group of which the amino group is optionally monosubstituted or disubstituted by an alkyl group, and the radical R$_2$ can also denote a phenyl group or a phenyl group substituted by an alkyl, hydroxyl or amino group, and Z denotes methyl, or a cosmetically acceptable salt thereof, wherein each of said alkyl groups contains 1–4 carbon atoms and each of said alkoxy groups contains 1–2 carbon atoms.

* * * * *